United States Patent [19]

Immel et al.

[11] Patent Number: 5,023,226

[45] Date of Patent: Jun. 11, 1991

[54] RUTHENIUM SUPPORTED CATALYST, ITS PREPARATION AND ITS USE IN THE PREPARATION OF SUBSTITUTED OR UNSUBSTITUTED CYCLOHEXYLAMINE AND SUBSTITUTED OR UNSUBSTITUTED DICYCLOHEXYLAMINE

[75] Inventors: Otto Immel; Hans-Helmut Schwarz; Reinhard Thiel, all of Krefeld, Fed. Rep. of Germany

[73] Assignee: Bayer Aktiengesellschaft, leverkusen, Fed. Rep. of Germany

[21] Appl. No.: 294,836

[22] Filed: Jan. 9, 1989

[30] Foreign Application Priority Data

Jan. 22, 1988 [DE] Fed. Rep. of Germany ....... 3801755

[51] Int. Cl.$^5$ .................. B01J 23/00; B01J 25/58; C07C 85/24; C07C 87/36
[52] U.S. Cl. .................. 502/313; 502/330; 502/332; 502/333; 502/334; 564/450; 564/462
[58] Field of Search ............. 502/313, 330, 332, 333, 502/334, 344, 184, 243; 564/450, 462

[56] References Cited

U.S. PATENT DOCUMENTS

| | | | |
|---|---|---|---|
| 2,184,070 | 12/1939 | Bertsch | 564/450 |
| 3,196,179 | 7/1965 | Robinson | 564/450 |
| 3,636,108 | 1/1972 | Brake | 564/450 |
| 3,655,747 | 4/1972 | Sennewald et al. | 502/313 |
| 3,846,343 | 11/1974 | Erickson et al. | 502/334 |
| 4,049,584 | 9/1977 | Weissel | |
| 4,186,145 | 1/1980 | Weissel | 564/450 |
| 4,429,155 | 1/1984 | Göetz et al. | |

FOREIGN PATENT DOCUMENTS

| | | |
|---|---|---|
| 0001425 | 4/1979 | European Pat. Off. |
| 0053818 | 6/1982 | European Pat. Off. |
| 0053819 | 6/1982 | European Pat. Off. |
| 2232359 | 1/1975 | France |
| 2234922 | 1/1975 | France |
| 2298366 | 8/1976 | France |
| 0969542 | 9/1964 | United Kingdom |

*Primary Examiner*—H. M. Sneed
*Assistant Examiner*—Thomas Saba
*Attorney, Agent, or Firm*—Sprung Horn Kramer & Woods

[57] ABSTRACT

Substituted or unsubstituted cyclohexylamine and substituted or unsubstituted dicyclohexylamine can be produced by catalytic hydrogenation of substituted or unsubstituted aniline by using a ruthenium catalyst which in addition to ruthenium also contains palladium, platinum or palladium and platinum on a support from the group consisting of $Al_2O_3$ and aluminum spinel treated with chromium and manganese and containing the noble metals in a total amount of 0.05-5% by weight and a weight ratio of Ru:Pd, Ru:Pt, or Ru:Pd/Pt of 1:9-9:1. All percentages are based on the total weight of the catalyst.

18 Claims, 1 Drawing Sheet

RUTHENIUM SUPPORTED CATALYST, ITS PREPARATION AND ITS USE IN THE PREPARATION OF SUBSTITUTED OR UNSUBSTITUTED CYCLOHEXYLAMINE AND SUBSTITUTED OR UNSUBSTITUTED DICYCLOHEXYLAMINE

BACKGROUND OF THE INVENTION

The invention relates to a ruthenium catalyst on a support, a process for its preparation and a process for the preparation of substituted or unsubstituted cyclohexylamine and substituted or unsubstituted dicyclohexylamine by catalytic hydrogenation of substituted or unsubstituted aniline using such a catalyst.

It is known to prepare cyclohexylamine by hydrogenation under pressure of aniline. For this hydrogenation, cobalt catalysts containing a basic additive (GB No. 969,542) and also Raney cobalt (JP No. 68/03180) are used. According to U.S. Pat. No. 3,636,108, an alkali-moderated ruthenium catalyst on an inert support material is used for the ring hydrogenation of aromatic amino compounds, $NH_3$ and, if appropriate, a solvent being additionally used. A further process for the hydrogenation under pressure of aniline to give cyclohexylamine is described in DE-AS (German Published Specification) No. 1,106,319, in which likewise a ruthenium catalyst is used. In this process dicyclohexylamine which is also formed is added again to the starting material; the process is accompanied by significant losses caused by the simultaneous formation of cyclohexane. In contrast to the publications mentioned so far, EP No. 53,818 considers palladium-supported catalysts more favourable for the hydrogenation under pressure of aniline than ruthenium catalysts.

In the known hydrogenation processes under pressure of aniline, dicyclohexylamine is formed in addition to cyclohexylamine merely as a byproduct. To obtain dicyclohexylamine in larger amounts, it is prepared by separate processes. Thus, it can be produced, for example, by hydrogenation under pressure of diphenylamine using a ruthenium/$Al_2O_3$ catalyst (DE-AS (German Published Specification) No. 1,106,319). Furthermore, dicyclohexylamine is formed in the reaction of cyclohexanone with cyclohexylamine in the presence of palladium on carbon at a hydrogen pressure of 4 bar (FR No. 1,333,692). In a complicated process, dicyclohexylamine can be recovered from the hydrogenation product of aniline over a nickel catalyst by fractionated condensation. Some of the ammonia which is also formed is removed from the remaining mixture, and the residue is recycled in the reaction (German Patent Specification No. 805,518).

A common problem of all processes for the ring hydrogenation of aromatic amines is that in some cases there is a significant formation of cyclohexane as a waste product which cannot be used further. It was therefore desired to develop a novel process which is useful even on an industrial scale, by which both cyclohexylamine and dicyclohexylamine can be prepared in one reaction step in a desired ratio of amounts, in which the loss caused by the formation of cyclohexane is reduced and in which furthermore the life of the catalyst used is improved.

SUMMARY OF THE INVENTION

Surprisingly, it has been found that the requirements mentioned can be met by using the ruthenium supported catalyst characterized below, that is, characterized in particular by the noble metal combination of Ru/Pd, Ru/Pt or Ru/Pd/Pt.

The invention accordingly relates to ruthenium catalysts also containing palladium, platinum or palladium and platinum in addition to ruthenium on a support treated with chromium and manganese from the group consisting of $Al_2O_3$ and aluminum spinel, containing the noble metals in a total amount of 0.05–5% by weight and a weight ratio of Ru:Pd, Ru:Pt or Ru:Pd/Pt of 1:9 to 9:1, the percentages being based on the total weight of the catalyst.

DETAILED DESCRIPTION OF THE INVENTION

Based on the total weight of catalyst, the total amount of the noble metals is 0.05–5% by weight, preferably 0.05–3% by weight, particularly preferably 0.1–2% by weight. The weight ratio of Ru:Pd, Ru:Pt or Ru:Pd/Pt extends from 1:9–9:1, preferably 2:8–8:2, particularly preferably 3:7 to 7:3.

Furthermore, up to 20% of the total amount of ruthenium and palladium or platinum can be replaced by other noble metals from the group consisting of iridium, rhodium, silver and gold.

The catalyst according to the invention can further contain, again based on the total weight of the catalyst, 0.01–10% by weight, preferably 0.1–5% by weight, of a basic alkaline metal compound. Examples of such basic alkali metal compounds are the oxides, hydroxides, alcoholates or salts of weak acids of lithium, sodium, potassium, rubidium or cesium, preferably the hydroxides, alcoholates or salts of weak acids of lithium, sodium or potassium, particularly preferably of sodium or potassium. Weak acids are for example carbonic acid, acetic acid, formic acid and other acids whose alkali metal salts show an alkaline reaction and are furthermore those which are free of nitrogen, halogen, sulphur and other elements known as hydrogenation catalyst poisons. Examples of alcoholates are those of methanol, ethanol, propanol, butanol and other alcohols. However, the addition of a basic alkali metal compound to the catalyst according to the invention is not absolutely necessary.

The catalyst according to the invention contains aluminum oxide or an aluminum spinel which has been treated with chromium and manganese. Suitable aluminum oxides are in particular the α- and the γ-modifications. Aluminum spinels are compounds of the formula Me(II)$Al_2O_4$ in which Me(II) is a divalent metal cation of iron, zinc, nickel, copper, cobalt, cadmium, magnesium or other metals, preferably of magnesium; $LiAlO_2$ (lithium/aluminum spinel) is also suitable. The aluminum can be replaced in part by iron, chromium or manganese. Such a support has a combined chromium and manganese content of about 0.05–8% by weight, preferably 0.2–5% by weight, based on the total weight of catalyst. The weight ratio of chromium and manganese is about 5:1 to 1:5, preferably 10:9 to 1:2. Such chromium- and manganese-treated supports are known from EP No. 208,933.

The catalysts according to the invention described can be prepared by applying compounds of chromium and manganese to an $Al_2O_3$ or an aluminum spinel in the form of extrudates, pills or balls having dimensions of about 2–10 mm, heating the support thus treated to an elevated temperature, then applying the noble metals and, if appropriate, the alkaline alkali metal compound separately and drying the support at 90°-130° C., if appropriate, in a vacuum.

The application of the chromium and manganese to the catalyst support can be carried out, for example, by coprecipitation of a manganese/chromium hydroxide mixture from a chromium and manganese salt solution using alkali metal hydroxide solution or ammonia and then, if appropriate, removing the soluble portions by washing with water. Suitable chromium and manganese salts are in particular the sulphates, chlorides, acetates and/or nitrates of the elements mentioned. The deposition of the chromium and manganese on the catalyst support can also be carried out in the form of ammonium/manganese chromate or ammonium/alkali metal/-manganese chromate from a solution of manganese(II) salts and ammonium dichromate by means of ammonia and/or basic alkali metal compounds. Particularly uniform and adhesive precipitations are obtained by adding the base slowly and evenly and avoiding large differences in the concentration. To this end, the precipitation can be carried out, for example, by means of urea under hydrolytic conditions, which ensures the conditions of slow addition of base in a particularly efficient manner. The chromium/manganese precipitate thus prepared is present as a shell on the support nucleus of $Al_2O_3$ or Al spinel.

After the application of the chromium and manganese compounds and the precipitation described, the catalyst support thus treated is washed until free of soluble compounds, before it is heated to elevated temperatures (about 200°-450° C., preferably 250°-350° C.). This heating is carried out over a period of 1-120 hours. During this time, the temperature can be increased within the range mentioned. After this heat treatment, the support treated with chromium and manganese is impregnated with the noble metals and, if appropriate, with the alkaline metal compounds. These can be done by first impregnating the support with the noble metals, for example in the form of aqueous solutions of their chlorides, nitrates, acetates or other suitable salts, after-drying the treatment with a solution of a basic alkali metal compound being carried out. In this treatment, the noble metals are precipitated in the form of their oxides or hydroxides. After a final drying process, the catalyst according to the invention is ready for use. Before being used, it is preferably activated in the reactor by treating it with hydrogen at elevated temperature of 150°-350° C. After deactivation, it may be desirable to remove anions such as chloride, nitrate, acetate or others by washing with water. This can be followed by another treatment with basic alkali metal compounds.

However, it is also possible first to impregnate the support with an alkali metal hydroxide solution, then to dry it and apply the noble metal salts mentioned to the catalyst support thus pretreated and made alkaline, precipitation of the noble metals in the form of their oxides or hydroxides taking place at the same time as the impregnation. In this case, too, the catalyst is ready for use after a final drying operation and can be activated, preferably before being used, with hydrogen at an elevated temperature in the manner described.

Depending upon whether or not the catalyst thus prepared is intended to contain the basic alkaline metal compounds, the subsequent water wash can be omitted or carried out.

Instead of applying the substances mentioned to the support mentioned by impregnation, it is also possible to spray it with suitable solutions. The required apparatuses in the adjustment in the level of substances used by choosing the amount and concentration of the solutions of the elements mentioned is known in principle to one skilled in the art.

The catalyst according to the invention is highly suitable for the ring hydrogenation of aniline under superatmospheric pressure. In a particularly surprising manner, by using the catalyst according to the invention, the amount of dicyclohexylamine which is also formed can be varied as a function of the hydrogenation temperature with respect to monocyclohexylamine, which allows a selective preparation of dicyclohexylamine in large amounts. Compared to a pure ruthenium catalyst which is prepared without the addition of palladium and/or platinum, the catalyst according to the invention exhibits the long life necessary for continuous industrial processes.

Thus, according to the invention a process for the preparation of a mixture of substituted or unsubstituted cyclohexylamine and substituted or unsubstituted dicyclohexylamine by hydrogenation of substituted or unsubstituted aniline with hydrogen in the presence of the catalyst described above is possible, which process is carried out in the range from 80° to 240° C., preferably 100° to 200° C. at a pressure from 50 to 500 bar, preferably 100 to 400 bar, particularly preferably 150 to 350 bar.

According to the invention, the amount of the desired dicyclohexylamine can be obtained by variation of the temperature, higher hydrogenation temperatures corresponding to a higher percentage of dicyclohexylamine and vice versa. Thus, for example, at a reaction temperature of about 100° C., only up to about 4% by weight of dicyclohexylamine are obtained in the mixture of the ring hydrogenated amines, while at a hydrogenation temperature of about 200° C. an amount of up to more than 50% of the hydrogenated amines can be present in the form of dicyclohexylamine.

The hydrogenation of the catalyst according to the invention can be carried out batchwise or continuously, preferably continuously; this hydrogenation is carried out in a trickle phase using a catalyst arranged in a fixed bed. The space velocity through the catalyst is set to 0.05 to 2, preferably 0.1 to 0.5 kg of aniline per liter of catalyst per hour. A small change in the dicyclohexylamine percentage obtained caused by changed activity of the catalyst over long reaction periods can be balanced by a small adjustment of the reaction temperature or of the other parameters. These conditions can be monitored by analysis of the reaction mixture.

The starting materials in the context of the following equation are aniline and substituted anilines which are converted into the corresponding cyclohexylamines and dicyclohexylamines:

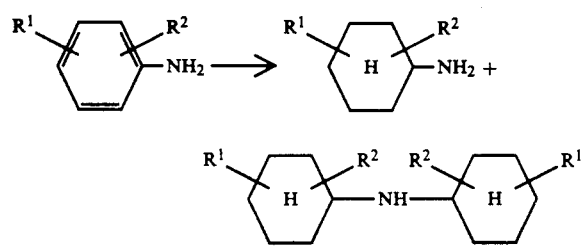

The radicals $R^1$ and $R^2$ independently of one another denote hydrogen, $C_1$–$C_4$-alkyl or $C_1$–$C_4$-alkoxy. Examples of the alkyl and alkoxy substituents mentioned are: methyl, ethyl, propyol, isopropyl, butyl, isobutyl, methoxy, ethoxy, propoxy, isopropoxy, butoxy or isobutoxy. Preferably, the substituents mentioned have 1–2 C atoms, particularly preferably they are methyl or methoxy. In a further preferred manner, one of the substituents $R^1$ and $R^2$ denotes hydrogen, while the other denotes alkyl or alkoxy of the type defined. Particularly preferably, the process is aimed at the ring-hydrogenation of unsubstituted aniline.

Cyclohexylamines and dicyclohexylamines of the type defined are used for the preparation of anti-ageing agents for synthetic rubbers and plastics, anticorrosives and also as precursors for plant-protection agents and textile aids.

EXAMPLE 1

(Preparation of the catalyst support according to EP No. 208,933)

100 g of spherical $\gamma$-$Al_2O_3$ having a diameter of 2–5 mm and a specific surface area of 350 m$^2$/g were initially introduced into a round-bottomed flask, and a solution of 8.3 g of $MnSO_4 \times 4\ H_2O$, 6.2 g of $(NH_4)_2Cr_2O_7$ and 45 g of urea in 72 ml of water was added. The flask was maintained at 85° C. for 1 hour with swirling, the unabsorbed liquid was filtered off, the catalyst support was washed until free from sulphate and then dried at 110° C. over a period of 25 hours in an aspirator vacuum. The catalyst support thus treated was then subjected to a heat treatment at 300° C. for 20 minutes.

EXAMPLE 2

200 g of a $\gamma$-aluminum oxide coated with Cr and Mn according to Example 1 were impregnated with a solution which had been prepared from 2.05 g of $RuCl_3$ and 1.67 g of $PdCl_2$ in 66 g of $H_2O$. The impregnated catalyst was dried at 120° C. and then activated in a hydrogen stream at 250° C. for 2 hours.

25 ml (20.5 g) of the catalyst thus prepared were used for the hydrogenation of aniline in a 250 ml shaker-autoclave, which on the inside was equipped with a centrally located wire basket firmly connected with the autoclave, which basket was charged with the catalyst. By means of this catalyst charge, 50 g each of aniline were hydrogenated at a hydrogen pressure of 280 bar at different temperatures. The hydrogenation time was in all cases of this series 3 hours. The hydrogenation products were analysed by gas chromatography and showed the following composition as a function of the hydrogenating temperature:

| Temperature (°C.) | 200 | 180 | 160 | 110 |
|---|---|---|---|---|
| Dicyclohexyl-amine (%) | 54.9 | 23.0 | 12.3 | 6.4 |
| Byproduct (%) | 0.27 | 0.2 | 0.1 | 0 |
| Cyclohexylamine (%) | Balance | Balance | Balance | Balance |

EXAMPLE 3

300 g of a $\gamma$-$Al_2O_3$ coated with Cr and Mn according to Example 1 were additionally heat-treated at 430° C. for 120 hours. 80 g of this heat-treated catalyst support were impregnated with a solution which had been prepared from 1.64 g of $RuCl_3$ and 1.34 g of $PdCl_2$ in 22.4 g of water. The impregnated catalyst support was activated in a hydrogen stream at 250° C. for 2 hours and then washed under running water until free from chloride and again dried at 120° C.

20.5 g (25 ml) of the catalyst thus prepared were used for the hydrogenation of aniline in a 250 ml autoclave in the manner described in Example 2. The hydrogenations also carried out at 280 bar gave the following results as a function of the hydrogenation temperature:

| Temperature (°C.) | 200 | 160 | 110 |
|---|---|---|---|
| Dicyclohexylamine (%) | 35.8 | 9.4 | 4.5 |
| Byproduct (%) | 0.17 | 0.14 | <0.1 |
| Cyclohexylamine (%) | Balance | Balance | Balance |

EXAMPLE 4

100 g of a $\gamma$-$Al_2O_3$ treated with Cr and Mn according to Example 1 were impregnated with a solution of 1.03 g of $RuCl_3$ and 0.83 g of $PdCl_2$ in 34.5 g of water and then dried at 120° C. The catalyst was then activated in a hydrogen stream at 250° C. for 2 hours.

25 ml (21 g) of this catalyst thus prepared were used for the hydrogenation of aniline in the autoclave at 280 bar. The procedure was carried out as in Example 2. The hydrogenation time in each of these experiments was 3 hours. The following product composition was obtained as a function of the hydrogenation temperature:

| Temperature (°C.) | 200 | 160 | 110 |
|---|---|---|---|
| Dicyclohexylamine (%) | 38.9 | 10.6 | 6.9 |
| Byproduct (%) | 0.2 | 0.1 | 0.1 |
| Cyclohexylamine (%) | Balance | Balance | Balance |

EXAMPLE 5

In further hydrogenation experiments, 60 ml (51.3 g) of the catalyst prepared in Example 3 were placed in a vertically arranged pressure tube (14 mm in diameter, 70 cm in length), which was heated by means of an oil thermostat. The interstitial volume was filled with fine sea sand (0.2 to 0.3 mm). At 280 bar, aniline and hydrogen were passed through the catalyst from above. The liquid trickled through the catalyst down to a separator. At the top of the separator, 20 l of hydrogen per hour were let down. The aniline throughput corresponded to a space velocity of the catalyst of 0.25 g of aniline/ml of catalyst×h and was kept constant.

The hydrogenation product was removed from the separator at regular intervals and analysed. The following product composition as a function of the time on-stream and the reaction temperature at a duration of the experiment of more than 9 months:

| Time onstream hours | Temperature °C. | Dicyclo-hexyl-amine % | Cyclo-hexyl-amine % | Byproduct % |
|---|---|---|---|---|
| 92 | 190 | 40.1 | 59.5 | 0.4 |
| 764 | 180 | 31.2 | 68.6 | 0.2 |
| 1,511 | 110 | 9.6 | 90.3 | 0.1 |
| 1,941 | 189 | 42.6 | 57.1 | 0.3 |
| 3,033 | 109 | 8.8 | 91.1 | 0.1 |
| 5,881 | 131 | 15.0 | 84.9 | 0.1 |
| 6,555 | 155 | 23.9 | 75.9 | 0.2 |

BRIEF DESCRIPTION OF THE FIGURE

The figure shows a diagram of the hydrogenation described in Example 6.

EXAMPLE 6

Figure 1:
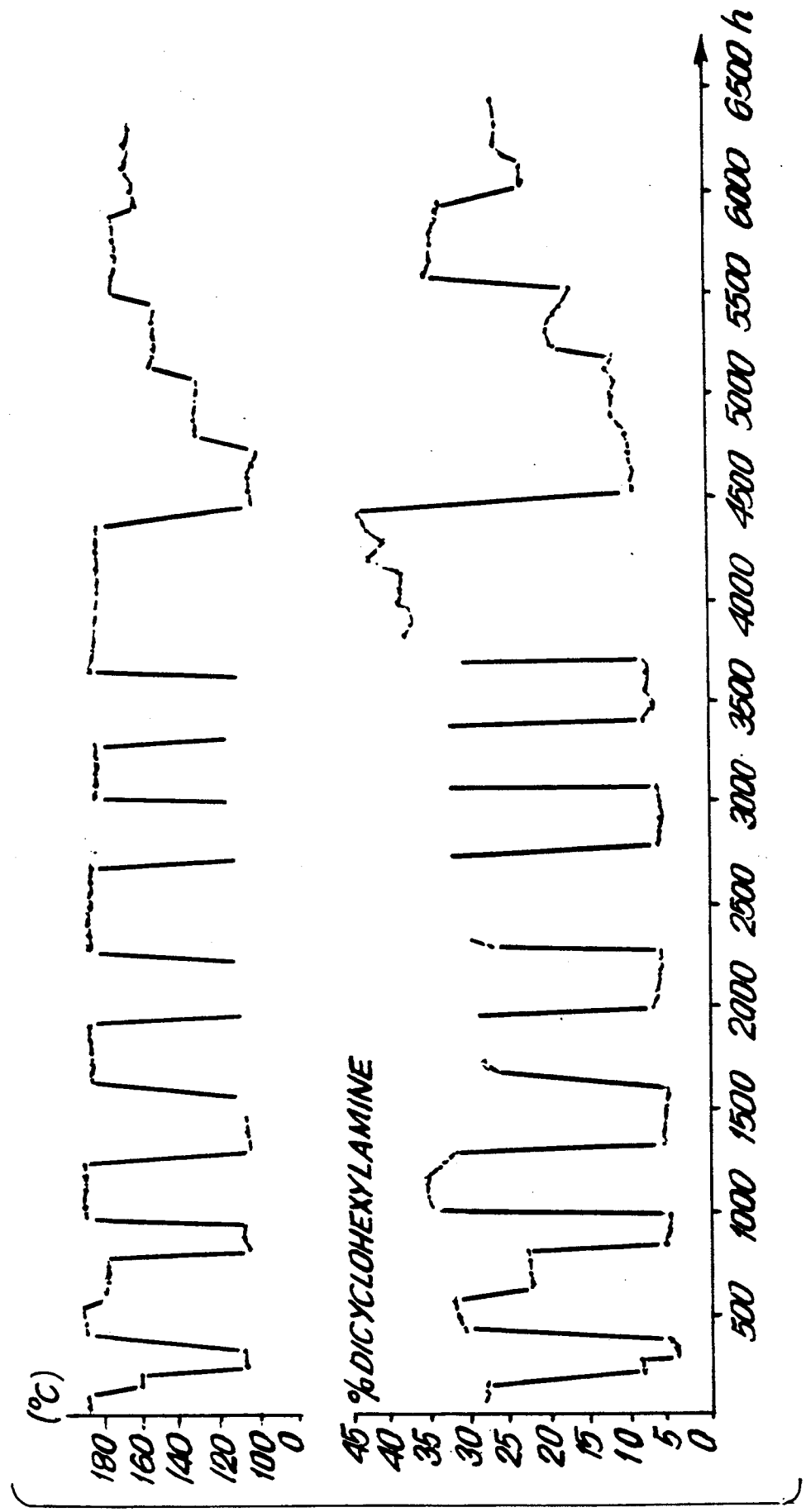

100 g of a $\gamma$-$Al_2O_3$ coated with Cr and Mn according to Example 1 were impregnated with a solution which had been prepared from 2.51 g of $Ru(NO_3)_3$, 0.33 g of $PdCl_2$ and 41 g of $H_2O$. The catalyst was subsequently activated in a hydrogen stream at 250° C. for 2 hours.

The continuous aniline hydrogenation was carried out by charging a pressure tube with 60 ml (50.7 g) of the catalyst thus prepared and following the procedure described in Example 5. During the entire duration of the experiment, the hydrogen pressure was 280 bar. The hydrogenation temperature was varied between 110° and 190° C. to control in this manner the dicyclohexylamine percentage in the reaction product. The space velocity of the catalyst was 0.25 g of aniline/ml×h. The aniline used was completely converted. The result of the hydrogenation obtained over a period of about 270 days has been evaluated in the form of a diagram in FIG. 1. The predetermined variation in temperatures and the corresponding dicyclohexylamine percentage determined has been plotted as a function of the time onstream of the catalyst. The balance (difference to 100%) essentially consisted of cyclohexylamine.

EXAMPLE 7

200 g of a $\gamma$-$Al_2O_3$ (balls, 2 to 5 mm in diameter) coated with Cr and Mn according to Example 1 were impregnated with a solution which had been prepared from 2.05 g of $RuCl_3$ and 3.33 g of $H_2PtCl_6$ in 58 g of water. The catalyst thus impregnated was dried at 120° C. and then activated in a hydrogen stream at 250° C. for 2 hours.

A 250 ml shaker-autoclave was charged with 25 ml (21 g) of the catalyst thus prepared, and the catalyst was used for hydrogenation under pressure (280 bar) of aniline at different temperatures as described in Example 2. At a constant hydrogenation time of 3 hours, the following product composition was obtained as a function of the temperature:

| Temperature (°C.) | 200 | 180 | 160 | 110 |
|---|---|---|---|---|
| Dicyclohexylamine (%) | 46.5 | 21.2 | 13.3 | 9.8 |
| Byproduct (%) | 0.50 | 0.30 | 0.2 | 0.1 |
| Cyclohexylamine (%) | Balance | Balance | Balance | Balance |

What is claimed is:

1. A Ruthenium catalyst also containing palladium, platinum or palladium and platinum in addition to ruthenium on a support treated with chromium and manganese from the group of $Al_2O_3$ and aluminum spinel containing the noble metals in a total amount of 0.05–5% by weight and a weight ratio of Ru:Pd, Ru:Pt, or Ru:Pd/Pt of 1:9–9:1, the percentages being based on the total weight of the catalyst.

2. The catalyst according to claim 1, characterized in that the noble metal content is 0.05–3% by weight.

3. The catalyst according to claim 2, characterized in that the nobel metal content is 0.1–2% by weight.

4. The catalyst according to claim 1, characterized in that the weight ratio of Ru:Pd, Ru:Pt, or Ru:Pd/Pt is 2:8–8:2.

5. The catalyst according to claim 4, characterized in that the weight ratio of Ru:Pd, Ru:Pt, or Ru:Pd/Pt is 3:7–7:3.

6. The catalyst according to claim 1, characterized in that up to 20% by weight of the total amount of ruthenium and palladium is replaced by other noble metals from the group consisting of iridium, rhodium, silver and gold.

7. The catalyst according to claim 1, characterized in that it contains 0.01–10% by weight, based on the total weight of the catalyst, of a basic alkali metal compound.

8. The catalyst according to claim 7, characterized in that the content of a basic alkali metal compound is 0,1–5% by weight.

9. The catalyst according to claim 7, characterized in that the basic alkali metal compounds are the oxides, hydroxides, alcoholates or salts of weak acids of Li, Na, K, Rb or Cs.

10. The catalyst according to claim 9, characterized in that the basic alkali metal compounds are the hydroxides, alcoholates or salts of weak acids of Li, Na or K.

11. The catalyst according to claim 1, characterized in that the treatment of the support with chromium and manganese is carried out up to a combined percentage of 0.05–8% weight, based on the total weight of the catalyst and the weight ratio of the elements chromium and manganese is set to 5:1–1:5.

12. The catalyst according to claim 11, characterized in that the combined chromium and manganese content is 0.2–5% by weight.

13. The catalyst according to claim 11, characterized in that the weight ratio of chromium and manganese is 10:9–1:2.

14. The catalyst according to claim 1, characterized in that it is treated with hydrogen at a temperature of 150°–350° C. prior to use.

15. A process for the preparation of a mixture of substituted or unsubstituted cyclohexylamine and substituted or unsubstituted dicyclohexylamine by hydrogenation of substituted or unsubstituted aniline with hydrogen in the presence of a ruthenium catalyst, characterized in that the ruthenium catalyst also containing palladium, platinum or palladium and platinum in addition to ruthenium on a support treated with chromium and manganese from the group consisting of $Al_2O_3$ and aluminum spinel containing the noble metals in a total amount of 0.05–5% by weight and a weight ratio of Ru:Pd, Ru:Pt, or Ru:Pd/Pt of 1:9–9:1, the percentages being based on the total weight of the catalyst is used and the reaction is carried out at 80°–240° C. at a pressure of 50–500 bar.

16. The process according to claim 15, characterized in that to increase the dicyclohexylamine percentage a higher temperature within the range of 80°–240° C. is chosen.

17. The process according to claim 15, characterized in that the space velocity of the catalyst is set to 0.05–2 kg of aniline per liter of catalyst per hour.

18. The process according to claim 15, characterized in that an aniline of the formula.

* * * * *